United States Patent [19]
Winter

[11] Patent Number: 5,814,996
[45] Date of Patent: Sep. 29, 1998

[54] LEAKAGE DETECTOR HAVING SHIELDED CONTACTS

[75] Inventor: Robert A. Winter, Sioux Falls, S. Dak.

[73] Assignee: Bowden's Automated Products, Inc., Viborg, S. Dak.

[21] Appl. No.: 832,193

[22] Filed: Apr. 8, 1997

[51] Int. Cl.⁶ .................................................. A61B 17/39
[52] U.S. Cl. ........................ 324/510; 324/72.5; 324/511; 340/650; 128/908; 606/35; 439/817; 439/819
[58] Field of Search .............................. 606/35; 128/908; 340/650; 439/817, 819; 324/510, 511, 72.5

[56] References Cited

U.S. PATENT DOCUMENTS

| | | | |
|---|---|---|---|
| 1,643,513 | 9/1927 | O'Brien | 439/817 |
| 2,189,714 | 2/1940 | Hilado | 439/817 |
| 3,806,860 | 4/1974 | Flammini | 439/817 |
| 5,175,493 | 12/1992 | Langgard | 324/72.5 |
| 5,312,401 | 5/1994 | Newton | 606/35 |
| 5,688,269 | 11/1997 | Newton | 606/35 |

*Primary Examiner*—Ernest F. Karlsen
*Assistant Examiner*—Jose M. Solis
*Attorney, Agent, or Firm*—Patnaude, Videbeck & Marsh

[57] ABSTRACT

The noise received by the unused connectors limits the accuracy of a device for measuring the leakage from a piece of electronic medical equipment. To reduce noise the device is surrounded by a Faraday shield which encloses unused connectors of the device. The shielded connector includes a post having a transverse hole near its distal end. A coil spring surrounds the post end and is connected to the Faraday shield of the device. An insulated retainer prevents the distal end of the coil spring from extending beyond the end of the post. The retainer is compressed against the coil spring to expose the transverse hole when a lead is to be attached to the connector.

8 Claims, 5 Drawing Sheets

LEAKAGE DETECTOR HAVING SHIELDED CONTACTS

The present invention relates to electronic testing equipment to detect electrical leakage in medical equipment, and specifically to equipment for measuring leakage to the leads which connect to patients, such as the leads to an electrocardiogram. More specifically, the present invention relates to improved shielding against electrostatic noise to reduce the percentage of error in the readings provided by such machines.

BACKGROUND OF THE INVENTION

Electronic equipment used in the medical industry has reached a level of sophistication in which all major manufacturers of the equipment are competing in an international market. Not only is the market of the equipment international, but the medical industry has now established international standards for testing such equipment. Accordingly, a manufacturer of medical equipment who desires to sell his products in Europe must provide equipment which meets the international standards.

There are international standards for leakage of electronic equipment having leads which are brought in contact with patients. For example, an electrocardiogram machine typically has ten leads which are attached to the body of a patient, and during the course of a test, the electrocardiogram machine measures input received from those leads. Since the leads connect to the equipment, any leakage which occurs between the leads and ground or between any combination of adjacent leads, could cause shock and injury to a patient.

To insure that electronic equipment will not cause such injury, the international standards require that equipment having leads which attach to a patient be regularly tested to insure that any leakage to the leads do not exceed certain maximums. According to the standards, a number of tests must be conducted for each piece of equipment. First, the equipment must be tested for leakage between the leads and ground. This test requires that each individual lead be tested for leakage through a simulated body load to ground and then that all the patient leads be connected together and the combined leads tested for leakage to ground.

In a second test, AC voltage is applied to the patient leads, and the amount of current is measured that the patient leads will draw or sink into the equipment. In this test, a source of AC power is applied through a protective resistor in series with a simulated body load to measure the current which the equipment will sink. Again, the test is first conducted on each of the individual leads and then all the leads are connected together for a combined test.

In a third test, the leads are tested for leakage to any conductive part of the equipment that a patient can touch. In this test, the individual leads are again connected through a simulated body load to a probe and the probe is contacted against all of the electrically conductive portions of the equipment that a patient can touch. As before, the test is first conducted with each of the leads, and then with all of the leads in combination.

In a fourth test, the leads are tested for leakage to other patient leads from the same piece of equipment. Again, the leads are connected to a test device having a simulated body load, first testing each lead for leakage with any one of the other leads of the equipment and then testing each lead for leakage to the combination of all the other leads of the equipment.

Because of the repetitious nature of the various tests, it is desirable to have an automated piece of test equipment which will accept all the leads of a piece of electronic equipment. The problem is that according to the international standards, the maximum allowable leakage current for any of the tests is no more than 10 microamps. It is also required that these low leakage currents be measured by the test equipment with an error of less than 5 percent. One of the problems with automating such tests is that the connectors to which the patient leads of a piece of equipment are to be connected act as miniature antenna, and collect stray noise which reduce the accuracy of the test equipment. Although many pieces of medical equipment employ a limited number of leads, an electrocardiogram machine employs 10 such leads, and a test equipment suitable for the medical industry must be capable of accepting the ten leads of an electrocardiograph machine.

Currently, the manufacturers of such test equipment provide for a manual adjustment to zero out stray leakage noise. However, the amount of noise received by such equipment is not constant. Noise levels are dependent upon the number of patient leads which are selected for use and upon environmental conditions, such as humidity and the emissions from surrounding electronic equipment. Because of the noise factor, existing manufacturers of test equipment have been unable to provide an automated device which can measure a 10 microamps leakage with an error of less than 5 percent as required by the international standards. Currently existing test equipment having the accuracy required to meet the international standards, therefore, has not been automated. Without automation, the testing of leads for low level leakage is a slow, tedious process. The industry, therefore, is in need of an automated testing device which can measure a leakage current for a piece of equipment having up to ten leads, and which can detect leakage as low as 10 microamps with an error of no greater than 5 percent.

SUMMARY OF THE INVENTION

Briefly, the present invention is embodied in an automated piece of equipment for measuring leakage in patient leads of a piece of medical or electronic equipment. In accordance with the present invention, the device has ten connectors to which patient leads may be connected, and the connectors are connected through an automated sequencing circuit to a test circuit. During the conduct of the first three tests, the automatic sequencing circuit first connects each of the ten connectors to the test circuit, then connects the combination of all ten connectors to the test circuit. During the fourth test, the sequencing circuit connects each of the individual ten connectors through the test circuit to each of the remaining nine connectors individually, and then to all nine remaining posts connected together. The sequencing circuit carries out the same sequencing for each of the ten connectors, while eliminating from the latter test configurations those which would be redundant to configurations conducted in earlier tests.

The test circuit includes a simulated body load and a microamp measuring circuit to measure the current passing through the simulated body load during each test. The test circuit further includes a second sequencing circuit whereby the measuring circuit is first connected in series with ground, second it is connected in series with a source of AC voltage and a protector resistor, third it is connected to a probe which can be contacted against the conductive surfaces of the equipment to be tested, and fourth to the remaining nine connectors to detect leakage between the connectors.

In accordance with the present invention, to reduce the reception of noise from unused connectors, each of the connectors has an electrically conductive center post having an outer surface and a distal end. Surrounding each of the posts and spaced from the outer surface of each such post is an electrically conductive coil spring having a distal end. At the distal end of the coil spring is an annular retainer which is longitudinally movable along the length of the center post from an extended position in which the distal end of the coil spring is substantially concentric with the distal end of the post, to retracted position wherein the spring is compressed, and the distal end of the spring is withdrawn from the distal end of the post. A stop is provided to prevent the annular retainer from moving beyond the distal end of the post, and the spring is electrically connected to a Faraday shield around the test device. Accordingly, when the spring and annular retainer is in the extended position, the spring provides a coaxial Faraday shield around the test post to reduce the noise received thereby. When a patient lead is to be connected to a connector of the present invention, the coil spring is compressed, and the annular retainer is withdrawn from around the distal end of the post such that a lead can be attached thereto. In the preferred embodiment, the post has a transverse hole perpendicular to the axis thereof through which the cylindrical end of a lead may be inserted. The cylindrical lead will be retained in the transverse hole by the spring forcing the annular retainer against the portions of the lead which extend outward of the transverse hole.

BRIEF DESCRIPTION OF THE DRAWINGS

A better understanding of the present invention will be had by a reading of the following description taken in connection with the drawings wherein.

DETAILED DESCRIPTION OF A PREFERRED EMBODIMENT

Figure 1:
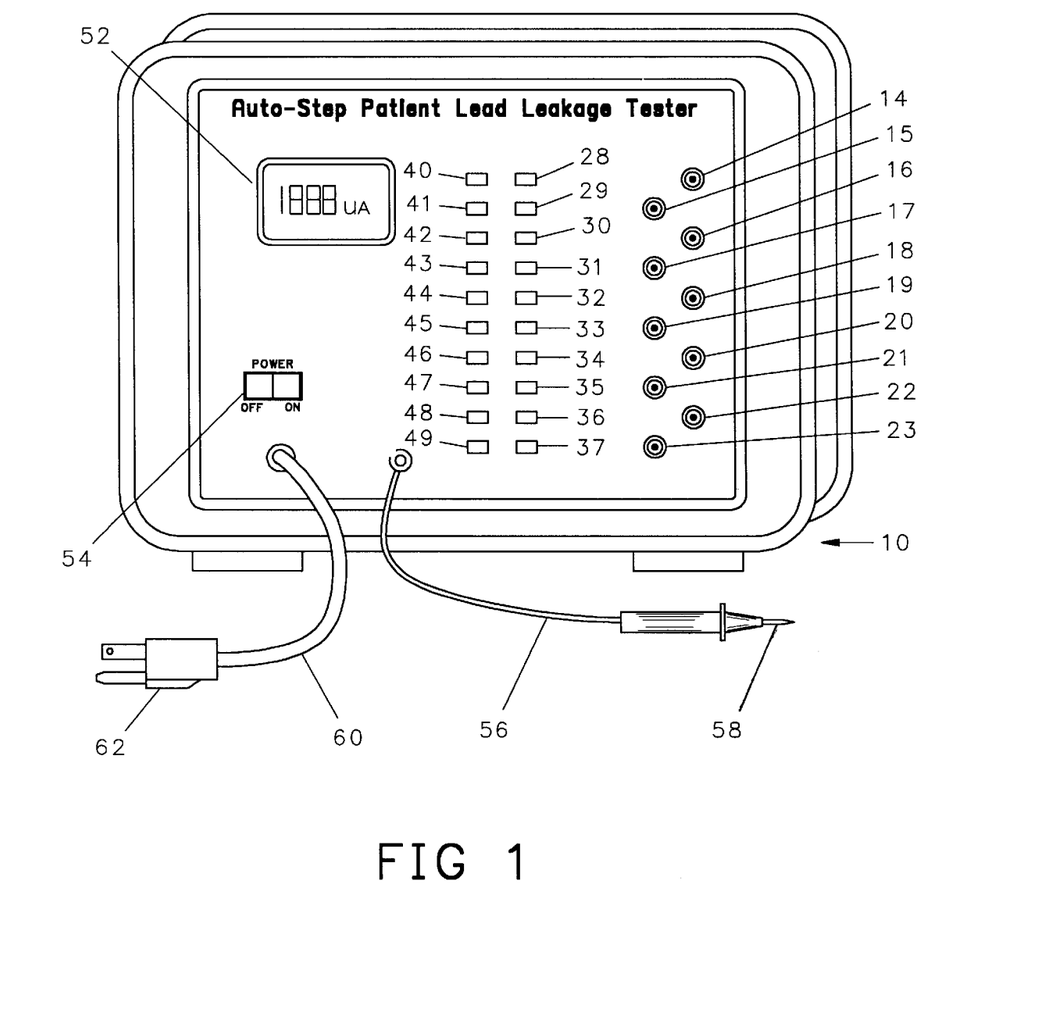
FIG. 1 is a frontal view of a test device in accordance with the present invention.

Referring to FIG. 1, an electronic leakage detecting A device 10 has a generally rectangular enclosure 12 on which are positioned ten connectors 14–23. Positioned adjacent each of the connectors 14–23 is an associated lead select button 28–37 respectively. Positioned adjacent the column of lead select buttons is a column of function buttons as follows: autostep select button 40, single step select button 41, each to ground select button 42, all to ground select button 43, sink each to ground select button 44, sink all to ground select button 45, each to probe select button 46, all to probe select button 47, each to each other select button 48, and each to all others select button 49. Buttons 40 and 41 are mechanically connected so that only one of these two buttons will be selected at any one time. Buttons 42 to 49 are similarly mechanically interconnected such that only one of eight can be selected at any one time. Finally, the lead select buttons 28 to 37 are not interconnected so that any combination of lead select buttons can be selected at a time.

Also positioned on the forward surface of the enclosure 12 is a readout 52 which displays leakage detected in microamps, and an on-off switch 54. Extending from the enclosure by an insulated lead 56 is a conductive probe 58. Also extending from the enclosure 12 is a power line 60 at the end of which is a conventional AC power connector plug 62.

Figure 2:
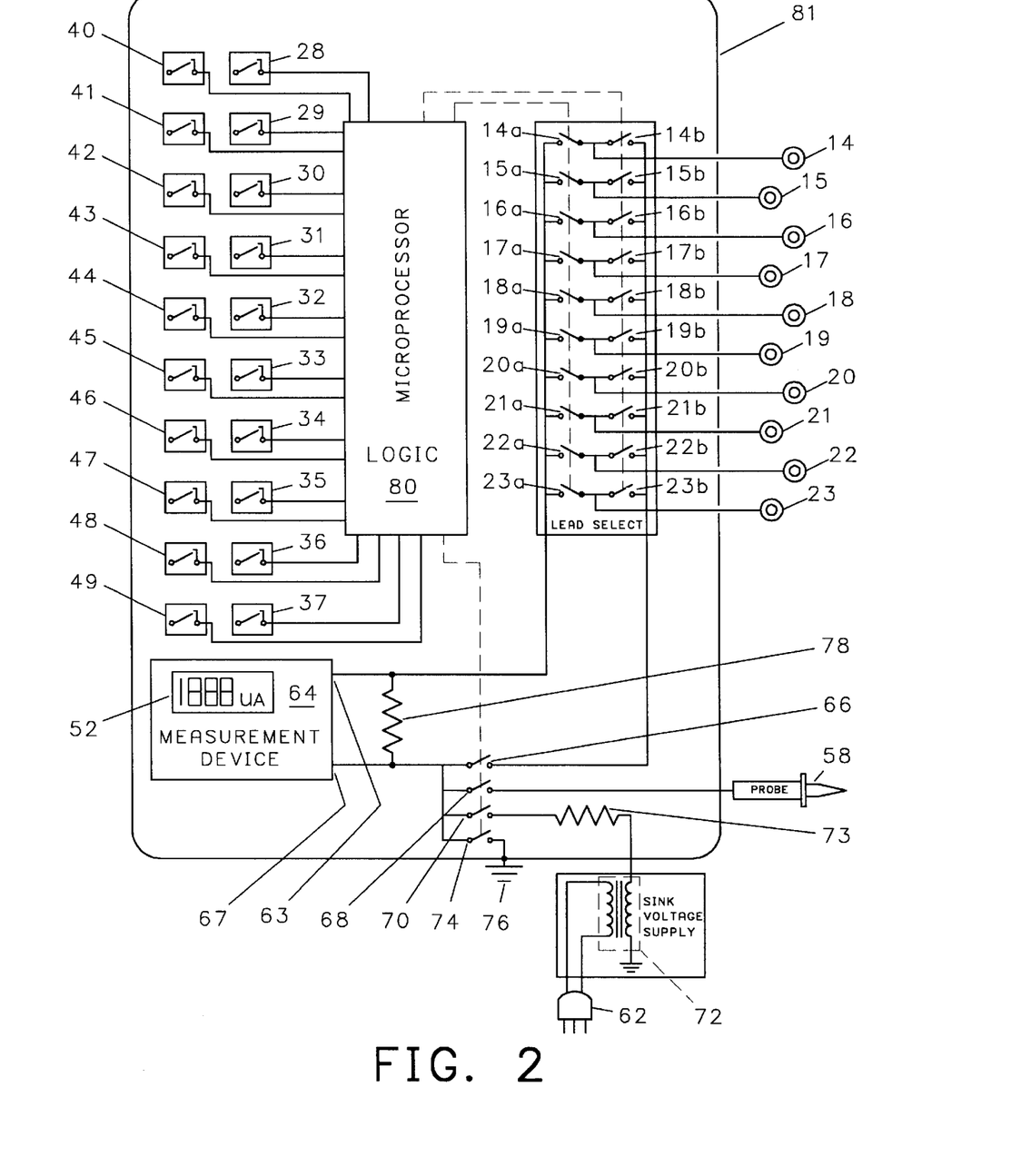
Fig. 2 is a schematic diagram of a circuit for the test device shown in FIG. 1.

Referring to FIG. 2, each of the connector posts 14–23 can be connected by an associated first switch 14a–23a to the positive terminal 63 of a measuring circuit 64, or may be connected by a second switch 14b–23b through a line switch 66 to the negative terminal 67 of the measuring circuit 64. A second line switch 68 connects or disconnects the conductive probe 58 to the negative side of the measuring circuit 64, a third line switch 70 connects the output from a transformer 72 through a protective resistor 73 to the negative terminal of the measuring circuit 64. Where the device 10 is adapted to receive 240 volts of AC power, the protection resistor 73 should be 100K ohms. As can be seen, the transformer 72 is driven by the AC current received through the power line 60. A fourth line switch 74 connects or disconnects the negative terminal of the measuring circuit 64 to ground 76.

Extending across the positive and negative terminals of the measuring circuit 64 is a simulated body load 78, which preferably is a 1000 Ohm resistor. All of the switches 14a–23a, 14b–23b, 66, 68, 70, 74 are operated by relays, not shown, and the functions are controlled by a logic 80 which may be a microprocessor. The opening and closing of all the various switches by the logic 80 is in response to instructions as received from the function switches operated by buttons 40–49. Surrounding the entire circuit is a Faraday shield 81 which is connected to ground 26.

To operate the device 10, an operator must depress one of the lower eight function buttons 42 to 49, which will instruct the logic 80 to configure the circuit as further described below. If the selected function button is for testing for leakage to individual leads attached to the connectors 14–23, which occurs by selecting one of buttons 42, 44, 46 or 48, then the operator must also select one of buttons 40 or 41. If button 40 is selected, the test of all the leads attached to the connectors will be automated by the logic 80 whereas if button 41 is selected, only one lead will be tested, that being the lead associated with the lead select button 28–37 which is also selected. By subsequently selecting in succession the remaining nine lead select buttons 29–37, all of the leads connected to the connectors 14–23 can be individually tested. When a lead is tested, any leakage detected will be displayed on the readout 52. When button 40 is selected for automated testing of the leads, only the highest leakage found in the test will be displayed on the readout 52.

Figure 3:
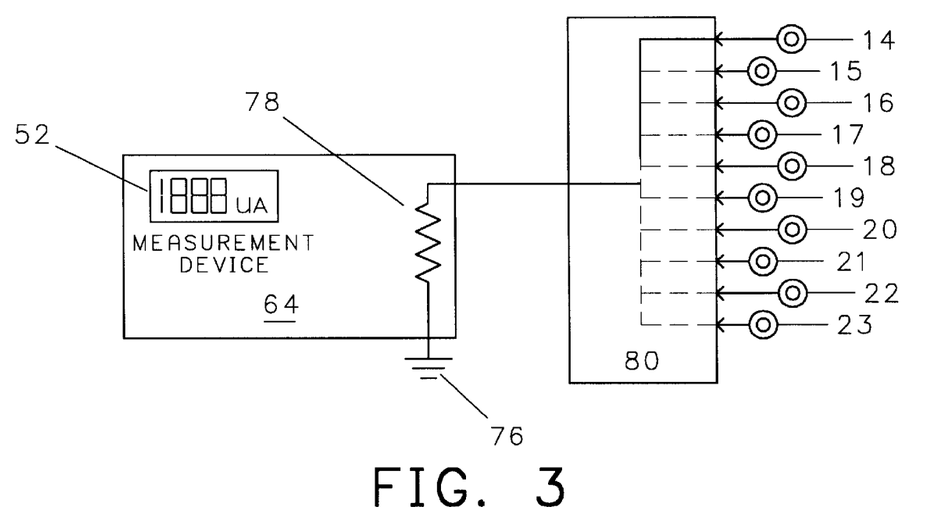
FIG. 3 is a simplified schematic diagram of the device shown in FIG. 1 configured to perform the first set of tests.

When the each to ground button 42 is selected, the logic 80 will cause line switch 66 to be closed and all the remaining switches to remain open thereby configuring the device as shown in solid lines in FIG. 3. The readout 52 will display any measured leakage between the leads through the body load 78 to ground 76. When the all to ground button 43 is selected, the logic 80 will cause the device to be configured as shown in the combined solid and broken lines in FIG. 3 such that the leakage to ground from all the leads combined will be measured.

Figure 4:
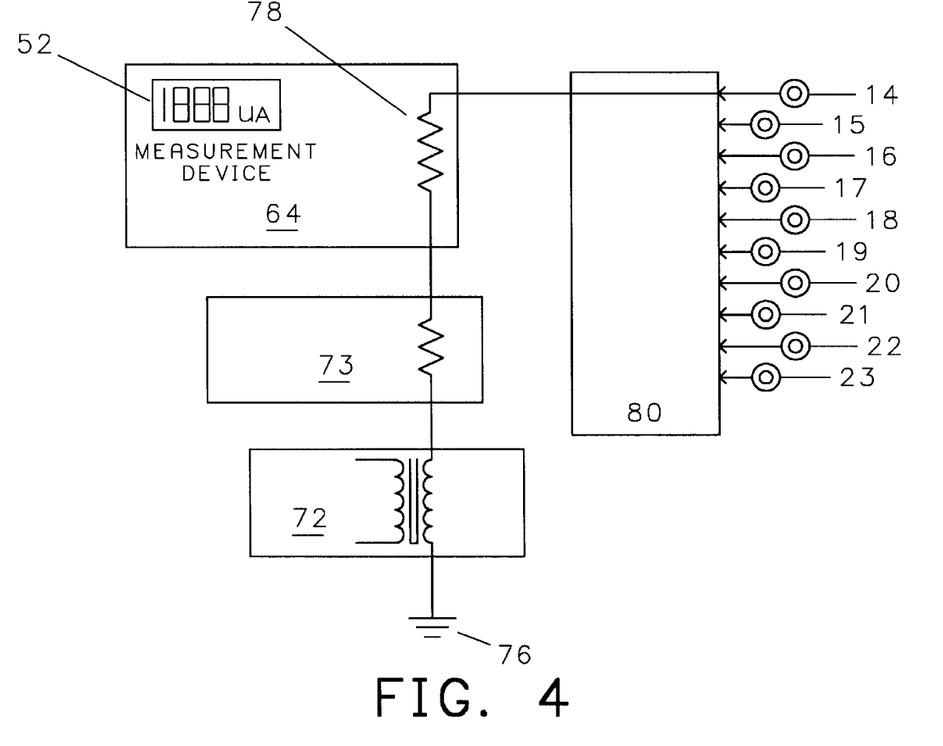
FIG. 4 is a simplified diagram of the test device of FIG. 1 configured to perform the second set of tests.

When the sink each to ground button 44 is selected, the logic 80 will cause the third line switch 70 to be closed and all other line switches opened, thereby configuring the device as shown in solid lines in FIG. 4. The readout 52 will display any measured leakage from the AC transformer 72, through the body load 78 into a lead attached to one of the connectors 14–23 When the sink all to ground button 45 is selected, the logic 80 will cause the device to be configured as shown in the combined solid and broken lines in FIG. 4 such that it will measure leakage to all the leads attached to the connectors 14–23 simultaneously.

Figure 5:
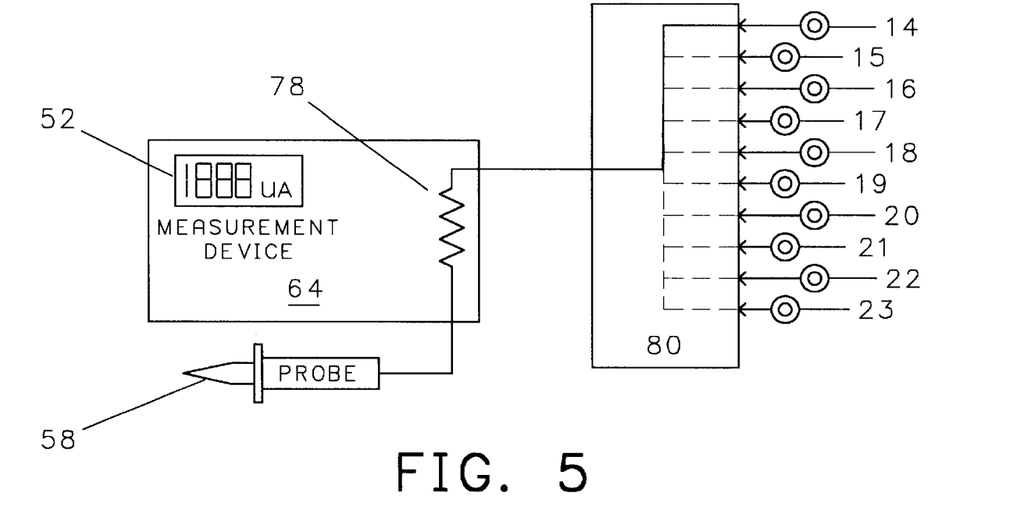
FIG. 5 is a simplified diagram of the test device shown in FIG. 1 configured to perform the third set of tests.

When the each to probe select button 46 is selected, the logic 80 will cause the second line switch 68 to be closed and all others opened thereby configuring the device as shown in solid lines in FIG. 5. In this configuration, the readout 52 will display any measured leakage from a surface contacted by the probe 58 through the simulated body load 78 to the leads attached to the connectors 14–23. When the all to probe button 47 is selected, the device to be configured as shown in the combined solid and broken lines in FIG. 5 such that it will measure leakage to all the leads attached to connectors 14–23 simultaneously.

Figure 6:
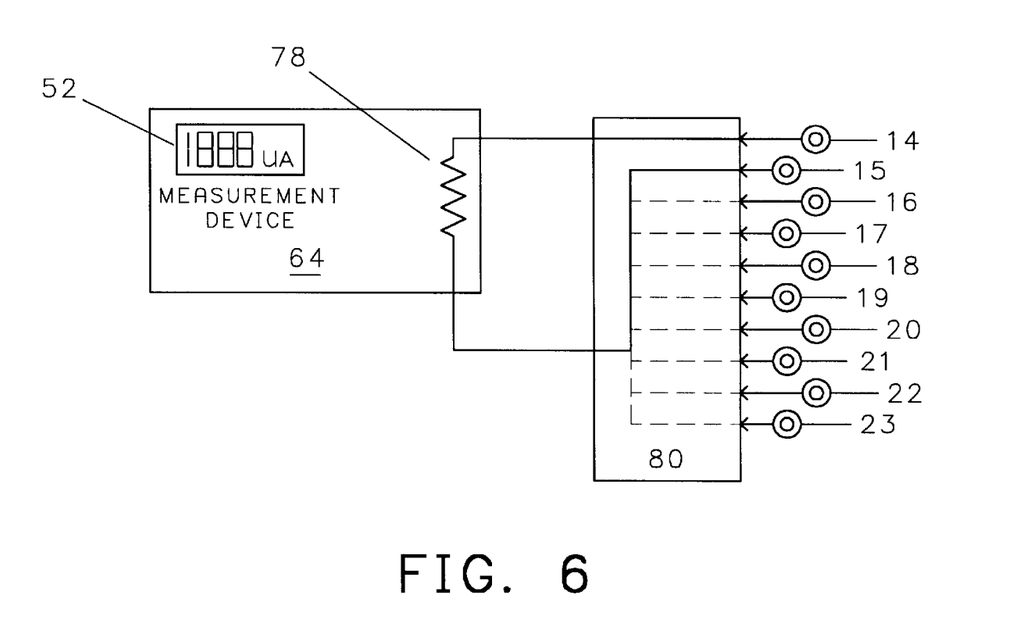
FIG. 6 is a test device shown in FIG. 1 configured to perform the fourth set of tests.

When the each to each other button 48 is selected, the logic 80 will cause the first line switch 66 to be closed and all others to be opened thereby configuring the device as shown in solid lines in FIG. 6. In this configuration, the device 10 will measure the leakage between any one lead attached to a connector 14–23, and one of the remaining leads attached to one of the connectors 14–23. When the each to all other button 49 is selected, the device 10 will be configured as shown in the combination of solid and broken lines in FIG. 6 and leakage from any one lead to all the remaining leads will be measured.

Referring to FIGS. 2, 7, 8 and 9, within the enclosure 12, and surrounding the circuit of the test device 10 is a Faraday shield 81 which shields the enclosed circuit from leakage noise. In the preferred embodiment, the enclosure 12 is made of metal and is connected to ground to provide the Faraday shield. As can be seen, the connectors 14–23 to which the patient leads are attached penetrate the Faraday shield 81 and may receive noise from the surrounding environment. In accordance with the present invention, each of the connectors 14–23 is shielded by a retractable extension of the Faraday shield.

Figure 7:
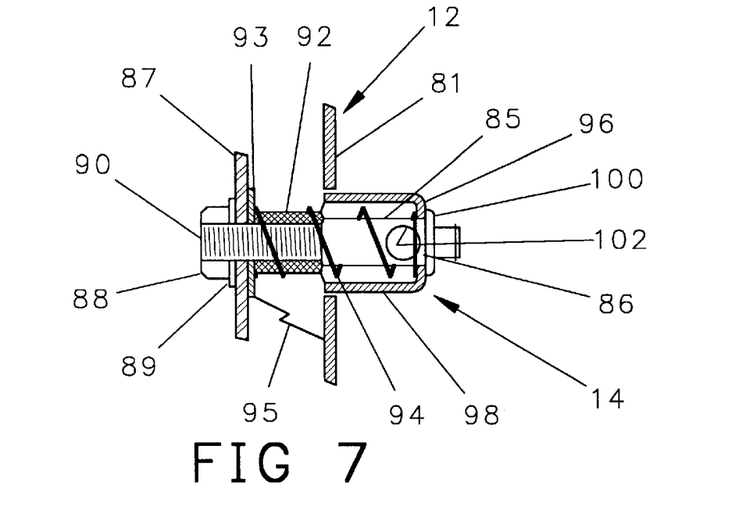
FIG. 7 is a cross-sectional view of a connector in accordance with the present invention with the spring in the extended position.
Figure 8:
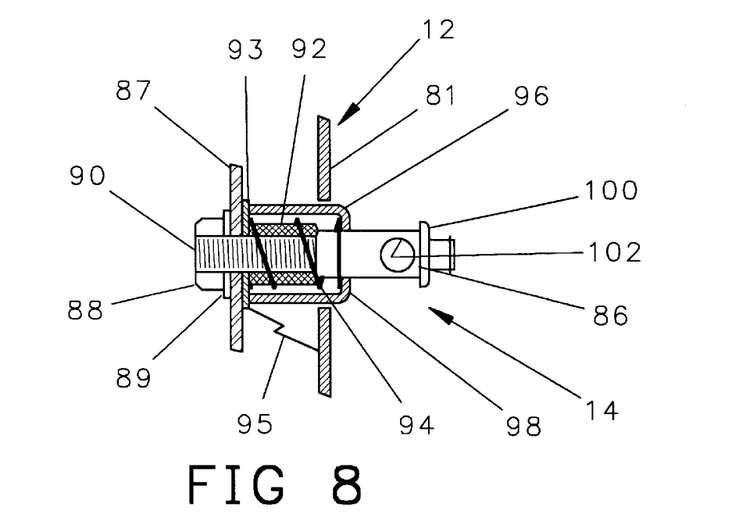
FIG. 8 is a cross-sectional view of the connector shown in FIG. 7 with the spring in the retracted position.
Figure 9:
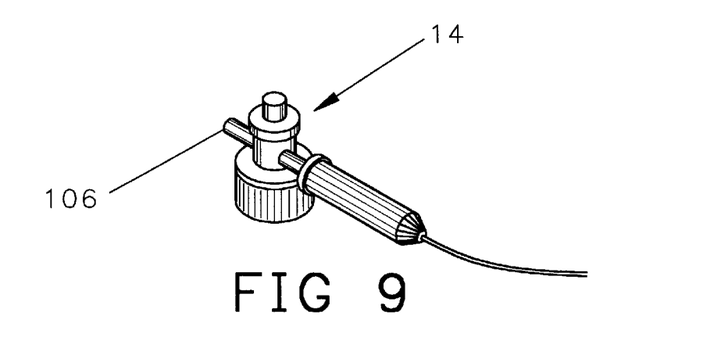
FIG. 9 is an isometric view of a patient lead connected to the connector shown in FIG. 7.

Connector 14, which is depicted in FIGS. 7, 8 and 9, is representative of all the connectors 14–23. As can be seen, the connector 14 includes a cylindrical post 85 having a distal end 86, and a threaded reduced diameter inner end 90 which extends through a printed circuit board 87 and is retained therein by a nut 88. A metal washer 89 on the inner surface of the circuit board 87 aids in electrically connecting the post 85 to a metal contact, not shown, on the circuit board 87.

Fitted around the reduced diameter portion 90 of the post 85 is an insulated tubular spacer 92 made of any suitable material such as sold under the trademark NYLON. As can be seen, between the inner end of the spacer 92 and the outer surface of the circuit board 87 is a second washer 93 which fits around a narrow inner end of the space 92 such that the washer 93 is insulated from the post 85. The outer diameter of the washer 93 is greater than the outer diameter of the spacer 92. Surrounding the outer surface of the spacer 92 is a coil spring 94 such that the inner surface of coil spring 94 is spaced from the outer surface of the post 85. The inner end of the coil spring is in contact with the second washer 93, and the washer 93 makes electrical contact with a land on the printed circuit, not shown, to electrically connect the coil spring 94 to the housing 12, and Faraday shield 81, the connecting being symbolically shown as wire 95.

Fitted over the distal end of the coil spring 94 is an annular insulated retainer 96 made of any suitable material such as sold under the trademark TEFLON. The retainer 96 also has a tubular lower body 98 which surrounds the upper portion of the coil spring 94. The distal end of the coil spring 94, therefore, abuts the inner surface of the retainer 96. The retainer 96 is prevented from sliding off the distal end of the post 14 by an enlarged non-conductive retaining ring 100 attached to the distal end 86 of the post 85. Extending transversely through the post 85 near the distal end 86 is a transverse hole 102 having a diameter suitably large to receive the distal end of a patient lead 106 as shown in FIG. 9.

The cylindrical sleeve 98 of the retainer 96 has a length which is shorter than the length of the portion of post 85 extending from the outer surface of the printed circuit board 87 to the distal end 86 thereof. Consequently, the retainer 96 can be moved axially inward along the post 90 to expose the transverse hole 102 and thereby permit a patient lead 106 to be inserted therein.

As can be seen, when the connector 14 is not in use, the coil spring 94 extends around the circumference of the post 85 with the distal end of the coil spring 94 positioned substantially concentric with the distal end 86 of the post 85 thereby extending the Faraday shield 81 along the length thereof. When the retainer 96 is moved axially inward to thereby depress the coil spring and expose the transverse hole 104 into which a patient lead 106 is connected, the connection penetrates the Faraday shield of the device.

A test device has, therefore, been disclosed whereby a piece of medical electronic equipment having up to ten patient leads may be tested for leakage employing an automated test. Furthermore, the test device of the present invention can be automated without requiring the device to be zeroed after each test to compensate for leakage arising from unused connector posts. It has been found that an automated testing device in accordance with the present invention can measure leakages as small as 10 microamp with an error of less than 5 percent as required by the international standards.

While the present invention has been disclosed in connection with one embodiment, it will be apparent to those skilled in the art that many changes and modifications may be made without departing from the true spirit and scope of the invention. It is the purpose of the appended claims to cover all such changes and modifications which fall within the true spirit and scope of the invention.

What is claimed:

1. A device for testing leakage from patient leads of a piece of electronic equipment, said device comprising, a leakage testing circuit, a Faraday shield around said testing circuit, said testing circuit comprising a plurality of connectors, each of said connectors for receiving a lead from a piece of equipment to be tested, a tubular Faraday shield around at least one of said connectors, said Faraday shield around said connector being electrically connected to said Faraday shield around said testing circuit, means for retracting said tubular Faraday shield to permit attachment of a lead to said connector.

2. A device in accordance with claim 1 and further comprising a logic for automating said testing.

3. A device in accordance with claim 2 wherein said device further comprises a simulated body load and means for measuring current through said body load.

4. A device in accordance with claim 3 wherein said testing circuit further comprises, a first testing circuit for testing for leakage from said patient leads to ground, a second testing circuit for testing sink leakage into said device from a source of current connected to said leads, a third testing circuit for testing for leakage from said lead to the outer surface of said piece of equipment being tested, and a fourth testing circuit for testing for leakage between said leads.

5. A device for testing leakage from patient leads of a piece of electronic equipment, said device comprising, an leakage testing circuit, a Faraday shield around said testing circuit, said testing circuit comprising a plurality of connectors, each of said connectors for receiving a lead from a piece of equipment to be tested, at least one of said connectors having a post with an outer surface and a distal end, said post being electrically connected to said testing circuit, an electrically conductive coil spring around said post, said coil spring having a distal end, an annular retainer on said distal end of said coil spring, said annular retainer longitudinally slidable along said post from an extended position wherein said distal end of said spring is substantially concentric with said distal end of said post, to a retracted position wherein said coil spring is compressed and said distal end of said post extends beyond said distal end of said coil spring, said coil spring having an inner surface spaced from said outer surface of said post, stop means for retaining said annular retainer from moving beyond said distal end of said post, and said coil spring being electrically connected to said Faraday shield of said device.

6. A device in accordance with claim 5 and further comprising a logic for automating testing.

7. A device in accordance with claim 6 wherein said device further comprises a simulated body load and means for measuring current through said body load.

8. A device in accordance with claim 7 wherein said testing circuit further comprises, a first testing circuit for testing for leakage from said patient leads to ground, a second testing circuit for testing sink leakage into said device from a source of current connected to said leads, a third testing circuit for testing for leakage from said lead to the outer surface of said piece of equipment being tested, and a fourth testing circuit for testing for leakage between said leads.

* * * * *

UNITED STATES PATENT AND TRADEMARK OFFICE
CERTIFICATE OF CORRECTION

PATENT NO. : 5,814,996

DATED : September 29, 1998

INVENTOR(S) : Robert A. Winter

It is certified that error appears in the above-identified patent and that said Letters Patent is hereby corrected as shown below:

Column 7, line 20, change "an" to --a--.

Signed and Sealed this

Ninth Day of March, 1999

Attest:

Q. TODD DICKINSON

*Attesting Officer*                *Acting Commissioner of Patents and Trademarks*